United States Patent [19]

Takatsu et al.

[11] Patent Number: 4,472,592
[45] Date of Patent: Sep. 18, 1984

[54] NEMATIC LIQUID CRYSTALLINE COMPOUNDS

[75] Inventors: Haruyoshi Takatsu, Kodaira; Hisato Sato, Tokyo, both of Japan

[73] Assignee: Dainippon Ink and Chemical, Inc., Tokyo, Japan

[21] Appl. No.: 507,916

[22] Filed: Jun. 27, 1983

[30] Foreign Application Priority Data

Jul. 9, 1982 [JP] Japan .................. 57-119481
Jul. 9, 1982 [JP] Japan .................. 57-119482
Jul. 28, 1982 [JP] Japan .................. 57-131836
Jul. 28, 1982 [JP] Japan .................. 57-131837

[51] Int. Cl.³ .................. C07C 69/90; C07C 69/75; C09K 3/34; G02F 1/13
[52] U.S. Cl. .................. 560/1; 252/299.6; 252/299.63; 252/299.64; 252/299.65; 350/350 R; 350/350 S; 560/61; 560/72; 560/73; 560/105; 560/107; 560/108
[58] Field of Search .................. 252/299.63, 299.64, 252/299.65, 299.6; 560/1, 61, 73, 72, 105, 107, 108; 350/350 R, 350 S

[56] References Cited

U.S. PATENT DOCUMENTS

| | | | |
|---|---|---|---|
| 4,001,137 | 1/1977 | Steinstrasser | 252/299.64 |
| 4,065,489 | 12/1977 | Steinstrasser et al. | 252/299.65 |
| 4,222,888 | 9/1980 | Dubois et al. | 252/299.64 |
| 4,229,315 | 10/1980 | Krause et al. | 252/299.63 |
| 4,261,652 | 4/1981 | Gray et al. | 252/299.62 |
| 4,293,434 | 10/1981 | Deutscher et al. | 252/299.63 |
| 4,387,038 | 6/1983 | Fukui et al. | 252/299.63 |
| 4,387,039 | 6/1983 | Sugimori et al. | 252/299.63 |
| 4,393,258 | 7/1983 | Sato et al. | 252/299.63 |
| 4,400,293 | 8/1983 | Romer et al. | 252/299.63 |

FOREIGN PATENT DOCUMENTS

| | | | |
|---|---|---|---|
| 56501 | 7/1982 | European Pat. Off. | 252/299.61 |
| 72204 | 2/1983 | European Pat. Off. | 252/299.62 |
| 87032 | 8/1983 | European Pat. Off. | 252/299.63 |
| 90671 | 10/1983 | European Pat. Off. | 252/299.63 |
| 3201721 | 8/1982 | Fed. Rep. of Germany | 252/299.63 |

(List continued on next page.)

OTHER PUBLICATIONS

Heppke, G. et al., Mol. Cryst. Liq. Cryst., vol. 98, pp. 309–319 (1983).

*Primary Examiner*—Teddy S. Gron
*Attorney, Agent, or Firm*—Sherman & Shalloway

[57] ABSTRACT

A nematic liquid crytalline compound selected from the group consisting of compounds represented by the general formula

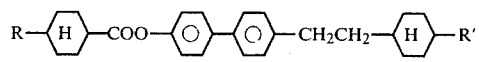

compounds represented by the general formula

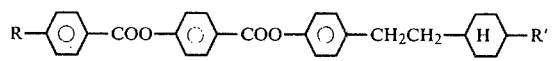

compounds represented by the general formula

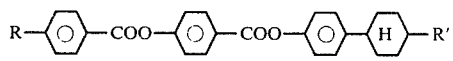

and compounds represented by the general formula

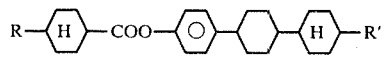

wherein R and R', independently from each other, represent a linear alkyl group having 1 to 7 carbon atoms, and each cyclohexane ring is arranged in a trans-(equatorial-equatorial) form. These compounds have higher nematic phaseisotropic liquid phase transition temperatures than conventional liquid crystalline compounds.

1 Claim, 4 Drawing Figures

FOREIGN PATENT DOCUMENTS

| | | | |
|---|---|---|---|
| 3237367 | 4/1983 | Fed. Rep. of Germany.. | 252/299.63 |
| 3208089 | 9/1983 | Fed. Rep. of Germany.. | 252/299.63 |
| 3211601 | 10/1983 | Fed. Rep. of Germany.. | 252/299.63 |
| 3318533 | 1/1984 | Fed. Rep. of Germany.. | 252/299.63 |
| 57-9742 | 1/1982 | Japan | 252/299.63 |
| 57-48945 | 3/1982 | Japan | 252/299.63 |
| 57-70839 | 5/1982 | Japan | 252/299.63 |
| 57-159742 | 10/1982 | Japan | 252/299.63 |
| 57-159743 | 10/1982 | Japan | 252/299.63 |
| 57-209252 | 12/1982 | Japan | 252/299.63 |
| 58-8022 | 1/1983 | Japan | 252/299.63 |
| 58-8023 | 1/1983 | Japan | 252/299.63 |
| 2092169 | 8/1982 | United Kingdom | 252/299.61 |

NEMATIC LIQUID CRYSTALLINE COMPOUNDS

This invention relates to novel nematic liquid crystalline compounds which are certain cyclohexanecarboxylic acid derivatives useful as electro-optical display materials.

The novel nematic liquid crystalline compounds provided by this invention are compounds of the general formulae (I)

(II)

(III)

and (IV)

In the above general formulae, R and R', independently from each other, represent a linear alkyl group having 1 to 7 carbon atoms, and each cyclohexane ring is arranged in a trans (equatorial-equatorial)form.

Typical liquid crystal display cells include, for example, a field effect mode cell proposed by M. Schadt et al. [Applied Physics Letters, 18, 127-128 (1971)], a dynamic scattering mode cell proposed by G. H. Heilmeier [Proceedings of the I.E.E.E., 56, 1162-1171 (1968)], and a guest-host mode cell proposed by G. H. Heilmeier [Applied Physics Letters, 13, 91 (1968)] or D. L. White [Journal of Applied Physics, 45, 4718 (1974)].

Liquid crystalline materials used in these liquid crystal display cells are required to have various properties. One important property required commonly of these display cells is that the liquid crystalline materials should have a nematic phase over a broad temperature range including room temperature. Many practical materials having this property are usually prepared by mixing at least one compound having a nematic phase near room temperature with at least one compound having a nematic phase at temperatures higher than room temperature. Many mixed liquid crystals of the above type now in practical use are required to have a nematic phase at least over an entire temperature range of from −30° C. to +65° C. In order to meet this requirement, it is the frequent practice to use compounds having a crystalline nematic phase transition temperature (C-N point) of about 100° C. and a nematic-isotropic liquid phase transition temperature (N-I) point of about 200° C., such as 4,4'-substituted terphenyl, 4,4'-substituted biphenylcyclohexane and phenyl 4,4'-substituted benzoyloxybenzoate.

In recent years, liquid crystal display cells have been used for multiple purposes (e.g., outdoor use), and the upper limit of the nematic temperature range has been required to be higher than +65° C. For this purpose, compounds having higher nematic phase-isotropic liquid phase transition temperatures (N-I points) than conventional compounds have been desired. The compounds of formulae (I), (II), (III) and (IV) in accordance with this invention meet this requirement. By mixing a small amount of such a compound with known liquid crystal mixtures, the nematic phase-isotropic liquid phase transition temperature of the liquid crystal mixtures can be greatly increased. Furthermore, since the compounds of formulae (I), (II), (III) and (IV) have very good compatibility with phenyl 4,4'-substituted cyclohexylcarboxylates which are disclosed in U.S. Pat. No. 4,372,871 as nematic liquid crystalline materials having excellent multiplexing drive characteristics, they can be mixed with these known compounds to give better mixed liquid crystals.

The compounds of formula (I) can be produced by the following process.

1st Step

The compound of formula (i) is reacted with anhydrous aluminum chloride in carbon disulfide or nitrobenzene to form the compound of formula (ii).

2nd Step

The compound of formula (ii) produced in the first step is reacted with hydrazine and potassium hydroxide in diethylene glycol or triethylene glycol to form the compound of formula (iii).

3rd Step

The compound of formula (iii) produced in the second step is reacted with an aqueous solution of hydro- gen iodide or an aqueous solution of hydrogen bromide in water or acetic acid to produce the compound of formula (iv).

4th Step

The compound of formula (iv) produced in the 3rd step is reacted with the compound of formula (v) in the presence of a basic compound such as pyridine as a catalyst in an inert organic solvent such as ether, benzene and toluene to produce the compound of formula (I).

The transition temperatures of the compounds of formula (I) so produced are summarized in Table 1.

TABLE 1

| No. | R | R' | Transition temperature (°C.) |
|---|---|---|---|
| 1 | n-C$_3$H$_7$— | n-C$_3$H$_7$— | 174(C→S) 195(S⇌N) 281(N⇌I) |
| 2 | n-C$_3$H$_7$— | C$_2$H$_5$— | 167(C→S) 170(S⇌N) 270(N⇌I) |
| 3 | n-C$_5$H$_{11}$— | n-C$_3$H$_7$— | 170(C→S) 195(S⇌N) 272(N⇌I) |
| 4 | n-C$_7$H$_{15}$— | C$_2$H$_5$— | 164(C→S) 222(S⇌N) 252(N⇌I) |
| 5 | n-C$_3$H$_7$— | n-C$_5$H$_{11}$— | 172(C→S) 203(S⇌N) 270(N⇌I) |
| 6 | n-C$_3$H$_7$— | n-C$_4$H$_9$— | 170(C→S) 182(S⇌N) 274(N⇌I) |

In Table 1, C represents a crystalline phase; S, a smectic phase; N, a nematic phase; and, I, an isotropic liquid phase (the same abbreviations are used in Tables 2, 3 and 4 below).

The compounds of formula (II) can be produced by reacting the compound of formula (vi) with the compound of formula (vii) in an inert organic solvent such as ether, benzene and toluene using a basic compound such as pyridine as a catalyst in accordance with the following reaction scheme.

The transition temperatures of the compounds of formula (II) so produced are summarized in Table 2.

TABLE 2

| No. | R | R' | Transition temperature (°C.) |
|---|---|---|---|
| 7 | n-C$_3$H$_7$— | C$_2$H$_5$— | 120(C→S) 122(S⇌N) 267(N⇌I) |
| 8 | n-C$_3$H$_7$— | n-C$_4$H$_9$— | 113(C→S) 117(S⇌N) 269(N⇌I) |
| 9 | n-C$_4$H$_9$— | n-C$_3$H$_7$— | 112(C→S) 116(S⇌N) 269(N⇌I) |
| 10 | n-C$_4$H$_9$— | n-C$_4$H$_9$— | 113(C→S) 121(S⇌N) 264(N⇌I) |
| 11 | n-C$_4$H$_9$— | C$_2$H$_5$— | 108(C→S) 111(S⇌N) 258(N⇌I) |
| 12 | n-C$_3$H$_7$— | n-C$_5$H$_{11}$— | 117(C→S) 125(S⇌N) 274(N⇌I) |
| 13 | n-C$_5$H$_{11}$— | C$_2$H$_5$— | 112(C→S) 118(S⇌N) 268(N⇌I) |

The compounds of formula (III) can be produced by reacting the compound of formula (vi) with the compound of formula (viii) in an inert organic solvent such as ether, benzene and toluene using a basic compound such as pyridine as a catalyst in accordance with the following reaction scheme.

The transition temperatures of the compounds of formula (III) so produced are summarized in Table 3.

TABLE 3

R―⬡―COO―⬡―COO―⬡―H―R'

| No. | R | R' | Transition temperature (°C.) |
|---|---|---|---|
| 14 | n-C$_3$H$_7$― | C$_2$H$_5$― | 139(C→S) 141(S⇌N) 289(N⇌I) |
| 15 | n-C$_3$H$_7$― | n-C$_4$H$_9$― | 133(C→S) 136(S⇌N) 291(N⇌I) |
| 16 | n-C$_3$H$_7$― | n-C$_5$H$_{11}$― | 138(C→S) 146(S⇌N) 293(N⇌I) |
| 17 | n-C$_4$H$_9$― | C$_2$H$_5$― | 127(C→S) 130(S⇌N) 280(N⇌I) |
| 18 | n-C$_4$H$_9$― | n-C$_3$H$_7$― | 132(C→S) 135(S⇌N) 292(N⇌I) |
| 19 | n-C$_4$H$_9$― | n-C$_4$H$_9$― | 133(C→S) 140(S⇌N) 287(N⇌I) |
| 20 | n-C$_5$H$_{11}$― | C$_2$H$_5$― | 132(C→S) 137(S⇌N) 290(N⇌I) |

The compounds of formula (IV) can be produced by reacting the compound of formula (v) with the compound of formula (ix) in an inert organic solvent such as ether, benzene or toluene using a basic compound such as pyridine as a catalyst in accordance with the following reaction scheme.

R―⟨H⟩―COCl (v)

HO―⬡―⬡―⟨H⟩―R' (ix)

↓

R―⟨H⟩―COO―⬡―⬡―⟨H⟩―R' (IV)

The transition temperature of the compounds of formula (IV) so produced are summarized in Table 4.

TABLE 4

R―⟨H⟩―COO―⬡―⬡―⟨H⟩―R'

| No. | R | R' | Transition temperature (°C.) |
|---|---|---|---|
| 21 | n-C$_3$H$_7$― | C$_2$H$_5$― | 186(C→S) 189(S⇌N) 308(N⇌I) |
| 22 | n-C$_3$H$_7$― | n-C$_3$H$_7$― | 194(C→S) 214(S⇌N) 319(N⇌I) |
| 23 | n-C$_3$H$_7$― | n-C$_4$H$_9$― | 190(C→S) 203(S⇌N) 313(N⇌I) |
| 24 | n-C$_3$H$_7$― | n-C$_5$H$_{11}$― | 191(C→S) 225(S⇌N) 309(N⇌I) |
| 25 | n-C$_5$H$_{11}$― | n-C$_3$H$_7$― | 189(C→S) 215(S⇌N) 311(N⇌I) |
| 26 | n-C$_7$H$_{15}$― | C$_2$H$_5$― | 182(C→S) 241(S⇌N) 289(N⇌I) |

The compounds of formulae (I) and (IV) are nematic liquid crystalline compounds having weak negative dielectric anisotropy. The compounds of formulae (II) and (III) are nematic liquid crystalline compounds having weak positive dielectric anisotropy. Hence, the compounds of formulae (I), (II), (III) and (IV) can be used as materials for dynamic scattering mode display cells when mixed, for example, with other nematic liquid crystalline compounds having negative or weak positive dielectric anisotropy. They can also be used as materials for field effect mode display cells when mixed with other nematic liquid crystalline compounds having strong positive dielectric anisotropy.

Typical examples of other nematic liquid crystalline compounds which can preferably be used in combination with the compounds of formula (I), (II), (III) or (IV) include phenyl 4,4'-substituted benzoates, phenyl 4,4'-substituted cyclohexanecarboxylates, biphenyl 4,4'-substituted cyclohexanecarboxylates, 4'-substituted phenyl 4(4-substituted cyclohexane carbonyloxy)benzoates, 4'-substituted phenyl 4(4-substituted cyclohexyl)benzoates, 4'-substituted cyclohexyl 4(4-substituted cyclohexyl)benzoates, 4,4'-biphenyl, 4,4'-phenylcyclohexane, 4,4'-substituted terphenyl, 4,4'-biphenylcyclohexane, and 2(4'-substituted phenyl)5-substituted pyrimidine.

Table 5 below summarizes the N-I points of various mixed liquid crystals composed of 90% by weight of matrix liquid crystals (A) now in widespread use as a nematic liquid crystalline material having excellent multiplexing drive characteristics and 10% by weight of compounds Nos. 1 to 6 of formula (I) shown in Table 1 respectively. Table 5 also shows the N-I point of the matrix liquid crystals (A) for comparison.

The matrix liquid crystal (A) are composed of 20% by weight of n-C$_3$H$_7$―⟨H⟩―⬡―CN, 16% by weight of n-C$_5$H$_{11}$―⟨H⟩―⬡―CN, 16% by weight of

-continued

TABLE 5

| | N—I Point |
|---|---|
| (A) | 54.0 |
| (A) + (No. 1) | 76.6 |
| (A) + (No. 2) | 75.4 |
| (A) + (No. 3) | 75.8 |
| (A) + (No. 4) | 73.7 |
| (A) + (No. 5) | 75.6 |
| (A) + (No. 6) | 75.9 |

Table 6 summarizes the N-I points of mixed liquid crystals composed of 90% by weight of the matrix liquid crystals (A) mentioned above and compounds Nos. 7 to 13 of formula (II) shown in Table 2 respectively, and for comparison, the N-I point of the matrix liquid crystals (A).

TABLE 6

| | N—I Point (°C.) |
|---|---|
| (A) | 54.0 |
| (A) + (No. 7) | 75.2 |
| (A) + (No. 8) | 75.4 |
| (A) + (No. 9) | 75.4 |
| (A) + (No. 10) | 75.0 |
| (A) + (No. 11) | 74.3 |
| (A) + (No. 12) | 75.9 |
| (A) + (No. 13) | 75.1 |

Table 7 summarizes the N-I points of mixed liquid crystals composed of 90% by weight of the matrix liquid crystals (A) mentioned above and compounds Nos. 14 to 20 of formula (III) shown in Table 3 respectively, and for comparison, the N-I point of the matrix liquid crystals (A).

TABLE 7

| | N—I Point (°C.) |
|---|---|
| (A) | 54.0 |
| (A) + (No. 14) | 74.4 |
| (A) + (No. 15) | 74.5 |
| (A) + (No. 16) | 74.7 |
| (A) + (No. 17) | 73.9 |
| (A) + (No. 18) | 74.7 |

TABLE 7-continued

| | N—I Point (°C.) |
|---|---|
| (A) + (No. 19) | 74.3 |
| (A) + (No. 20) | 74.5 |

Table 8 summarizes the N-I points of mixed liquid crystals composed of 90% by weight of the matrix liquid crystals (A) mentioned above and 10% by weight of compounds Nos. 21 to 26 of formula (IV) shown in Table 4 respectively, and for comparison, the N-I point of the matrix liquid crystals (A).

TABLE 8

| | N—I Point (°C.) |
|---|---|
| (A) | 54.0 |
| (A) + (No. 21) | 78.2 |
| (A) + (No. 22) | 79.4 |
| (A) + (No. 23) | 78.8 |
| (A) + (No. 24) | 78.3 |
| (A) + (No. 25) | 78.6 |
| (A) + (No. 26) | 76.6 |

It can be seen from the data given in Tables 5 to 8 that the addition of 10% by weight of the compounds of formulae (I), (II), (III) and (IV) can increase the N-I point of the mixed liquid crystals (A) by at least 20° C. The high utilitarian value of the compounds of this invention lies in the fact that by adding a small amount of each of these compounds, the upper limit of the operating temperature range can be increased.

The advantages brought about by the compounds of this invention are demonstrated by the following comparative experiments.

Comparative Experiment I

A known compound of the following formula used widely to increase the N-I points of mixed crystals was mixed in various proportions with the aforesaid matrix liquid crystals (A). Likewise, one compound of the invention represented by the following formula was mixed in various proportions with the matrix liquid crystals (A).

Figure 1:
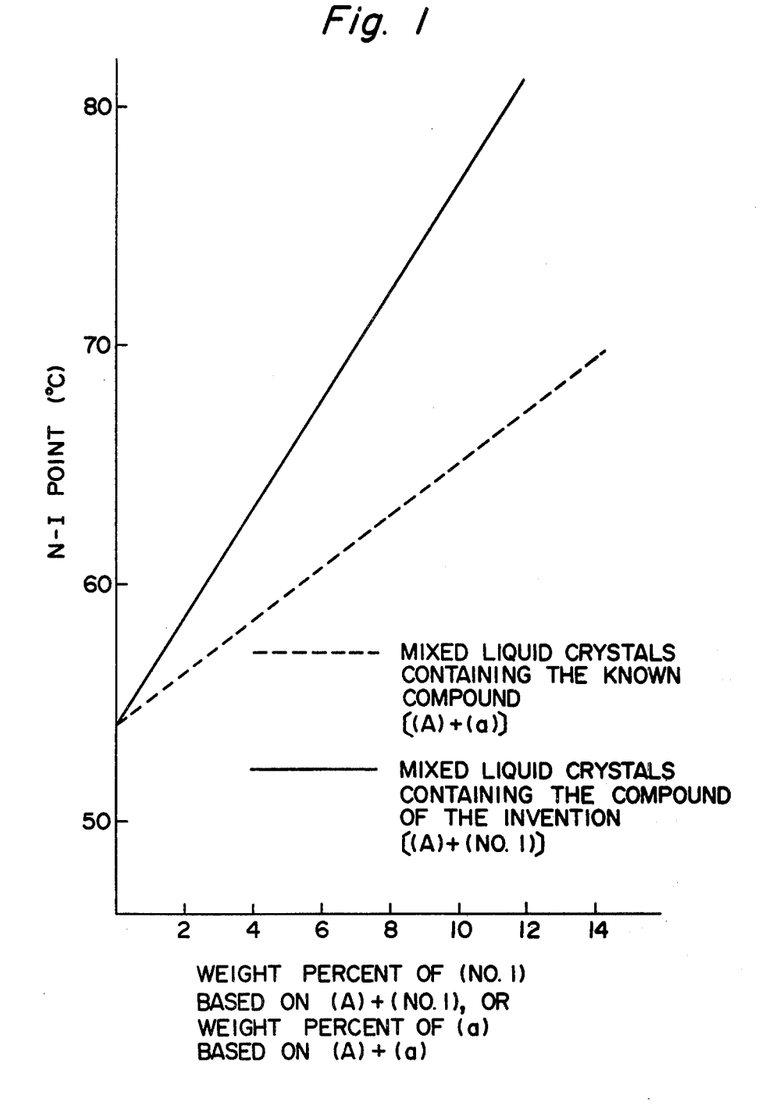
FIGS. 1 to 4 show the effect of the compounds of this invention on the N-I point relative to typical known analogous compounds when added in the same amounts.

The N-I points of the resulting two kinds of mixed crystals were measured, and on the basis of the results of the measurement, the relation between the N-I points and the amounts added was plotted in FIG. 1 of the accompanying drawings.

Comparative Experiment II

A known compound of the following formula used widely to increase the N-I points of mixed liquid crystals was mixed in various proportions with the aforesaid matrix liquid crystals (A). Likewise, one compound of the invention represented by the following formula (No. 10)

was mixed in various proportions with the matrix liquid crystals (A).

Figure 2:
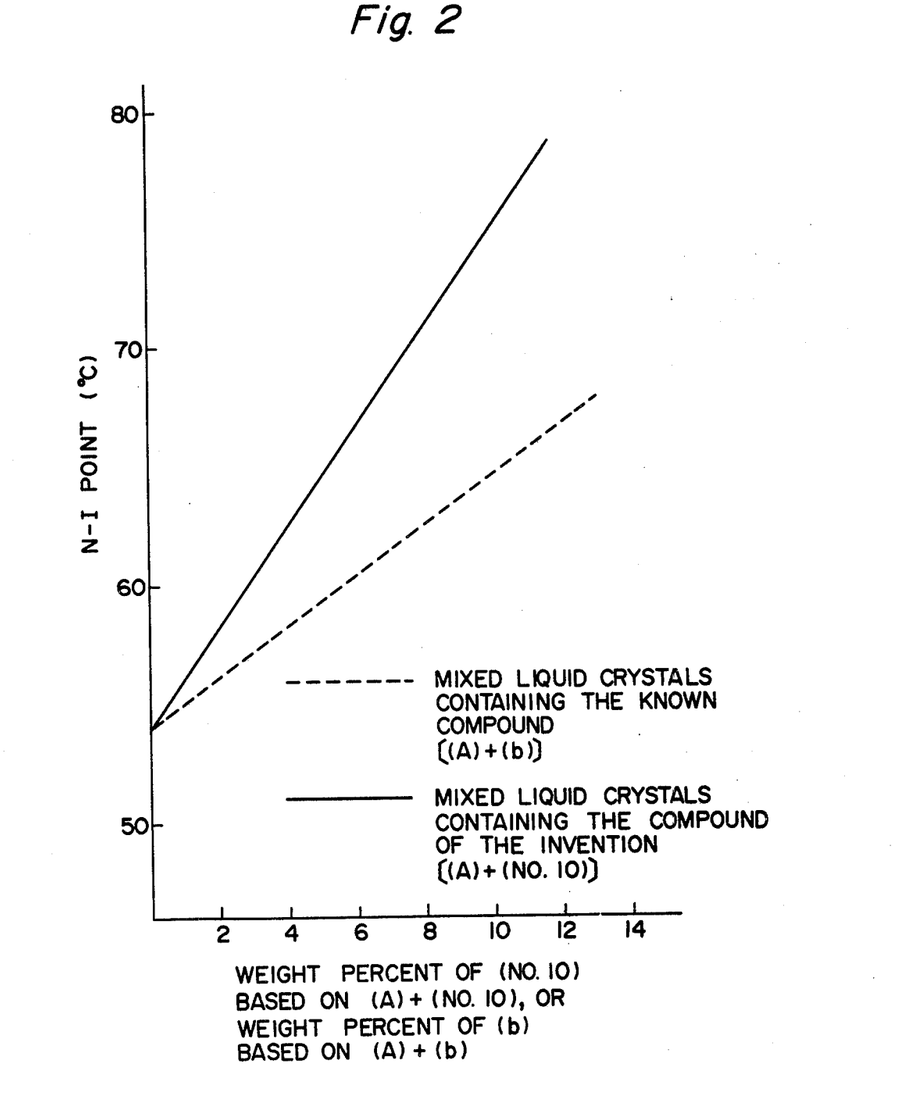

The N-I points of the resulting two kinds of mixed liquid crystals were measured, and on the basis of the results of the measurement, the relation between the N-I points and the amounts added was plotted in FIG. 2 of the accompanying drawings.

Comparative Experiment III

A known compound of the following formula (b)

widely used to increase the N-I points of mixed liquid crystals was mixed in various proportions with the aforesaid matrix liquid crystals (A). Likewise, one compound of the invention represented by the following formula (No. 19)

was mixed in various proportions with the matrix liquid crystals (A).

Figure 3:
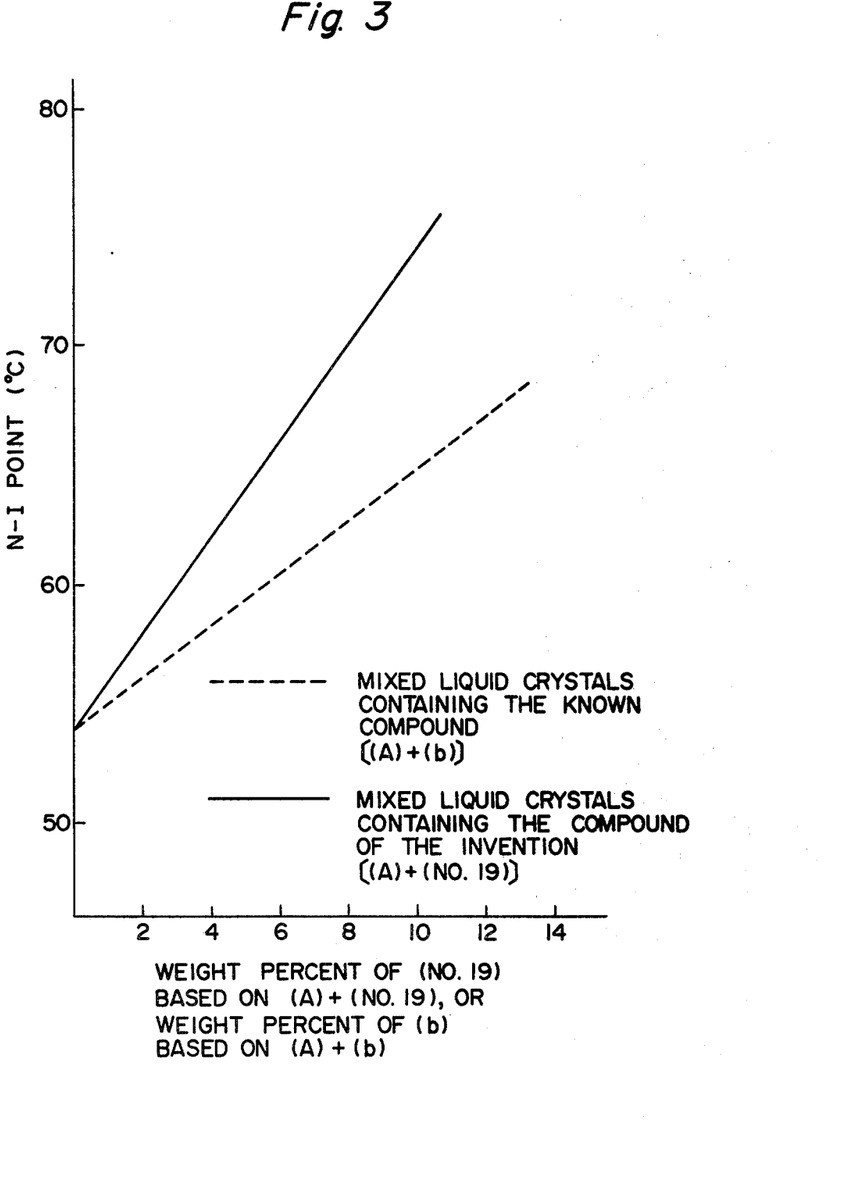

The N-I points of the resulting two kinds of mixed liquid crystals were measured, and on the basis of the results of the measurement, the relation between the N-I points and amount added was plotted in FIG. 3 of the accompanying drawings.

Comparative Experiment IV

A known compound of the following formula (c)

widely used to increase the N-I points of mixed crystals was mixed in various proportions with the matrix liquid crystals (A) mentioned above. Likewise, one compound of this invention represented by the following formula (No. 22)

was mixed in various proportions with the matrix liquid crystals (A).

Figure 4:
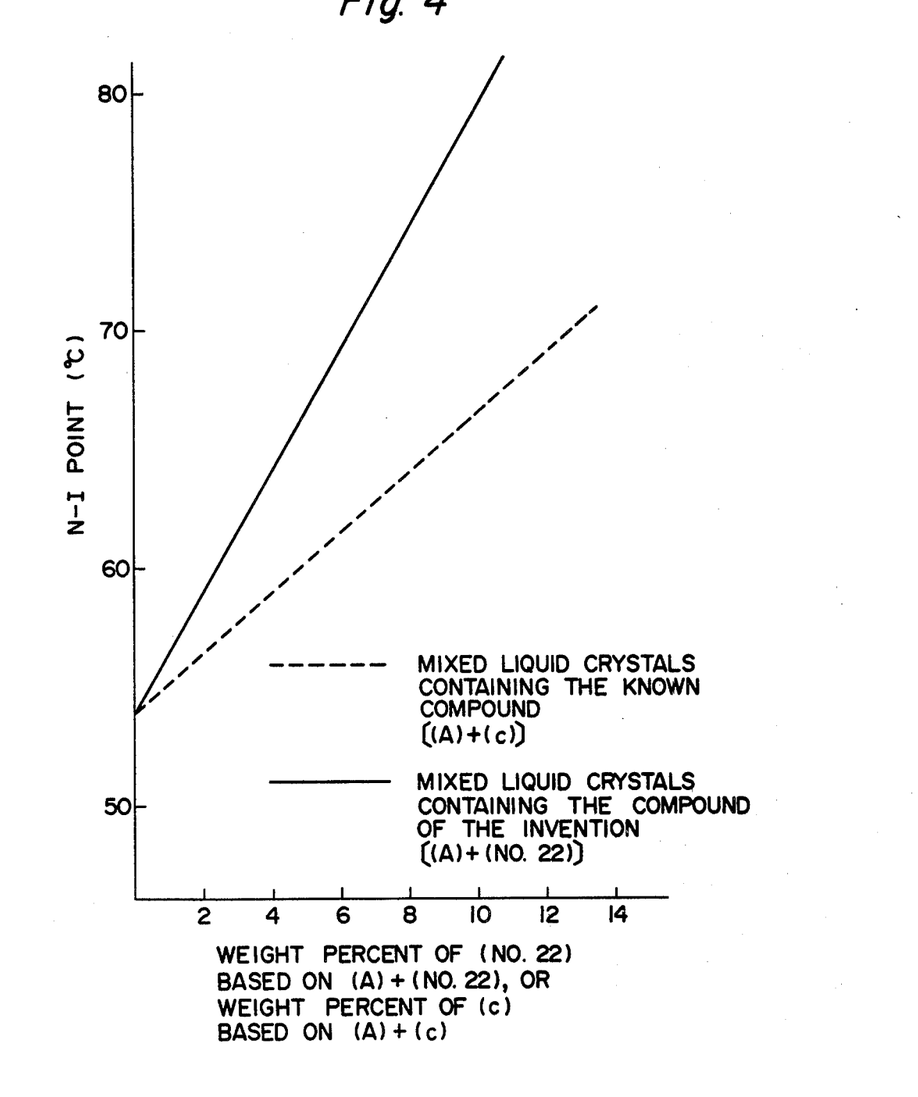

The N-I points of the resulting two kinds of mixed liquid crystals were measured, and on the basis of the results of the measurement, the relation between the N-I points and the amounts added was plotted in FIG. 4 of the accompanying drawings.

It will be understood from the facts shown in Comparative Experiments I, II, III and IV that the compounds of this invention increase the N-I point to a much greater extent than typical known analogous compounds when they are added in the same amounts.

EXAMPLE 1

Anhydrous aluminum chloride (16.0 g; 0.120 mole) was added to 100 ml of carbon disulfide, and with stirring at room temperature, 20.3 g (0.100 mole) of trans-4-n-propylcyclohexylacetyl chloride was added dropwise. The mixture was further stirred at room temperature for 1 hour. The mixture was then cooled to 5° C., and a solution of 18.4 g (0.100 mole) of p-methoxybiphenyl in 100 ml of carbon disulfide was gradually added dropwise. After the addition, the mixture was reacted at 10° C. for 3 hours. The reaction mixture was added to ice water. The mixture was heated to evaporate carbon disulfide. The residue was stirred at 60° C. for 1 hour. After cooling, the reaction product was extracted with toluene. The extract was washed with water and dried. Toluene was evaporated, and the residue was recrystallized from ether to give 15.8 g (0.0451 mole) of a compound of the following formula.

To the resulting compound were added 180 ml of triethylene glycol, 7.88 g (0.126 mole) of 80% hydrazine hydride and 10.1 g (0.153 mole) of 85% potassium hydroxide. With stirring, the temperature was gradually raised, and the mixture was reacted at 180° C. for 5 hours. After cooling, 200 ml of water and 80 ml of a 10% aqueous solution of sodium hydroxide were added. The mixture was extracted with ether, and the extract was washed with water. Ether was evaporated, and 100 ml of glacial acetic acid and 17 cc of a 47% aqueous solution of hydrogen bromide were added. The mixture was reacted at the refluxing temperature for 8 hours. After the reaction, the reaction mixture was cooled, and 200 ml of water was added. The mixture was extracted with ether. The extract was washed with water and dried over anhydrous sodium sulfate. Ether was evaporated, and the residue was recrystallized from n-hexane to give 10.6 g (0.0329 mole) of a compound of the following formula.

The resulting compound (10.6 g; 0.0329 mole) was dissolved in 70 ml of toluene, and 5.20 g (0.0658 mole) of pyridine was added. With stirring at room temperature, 6.20 g (0.0329 mole) of trans-4-n-propylcyclohexanecarbonyl chloride was added dropwise. After the addition, the mixture was reacted at the refluxing tem- perature for 3 hours. After the reaction, the reaction mixture was extracted with toluene. The extract was washed with water and dried. Toluene was evaporated, and the residue was recrystallized from acetone to give 12.7 g (0.0268 mole) of a compound of the following formula.

Yield: 26.8%
Transition temperatures: 174° C. (C→S)
195° C. (S⇌N)
281° C. (N⇌I)

EXAMPLE 2

By the same procedure as in Example 1, the following compound was obtained.

Yield: 25.3%
Transition temperatures: 167° C. (C→S)
170° C. (S⇌N)
270° C. (N⇌I)

EXAMPLE 3

By the same procedure as in Example 1, the following compound was obtained.

Yield: 26.2%
Transition temperatures: 170° C. (C→S)
195° C. (S⇌N)
272° C. (N⇌I)

EXAMPLE 4

By the same procedure as in Example 1, the following compound was obtained.

Yield: 25.7%
Transition temperatures: 164° C. (C→S)
222° C. (S⇌N)
252° C. (N⇌I)

EXAMPLE 5

By the same procedure as in Example 1, the following compound was obtained.

Yield: 27.1%
Transition temperatures: 172° C. (C→S)
203° C. (S⇌N)
270° C. (N⇌I)

EXAMPLE 6

By the same procedure as in Example 1, the following compound was obtained.

Yield: 26.3%
Transition temperatures: 170° C. (C→S)
182° C. (S⇌N)
274° C. (N⇌I)

EXAMPLE 7

23.2 g (0.100 mole) of a compound of the formula and 30.3 g (0.100 mole) of a compound of the formula were dissolved in 200 ml of toluene, and with stirring, 15.8 g of (0.200 mole) of pyridine was added dropwise. After the addition, the mixture was refluxed for 2 hours. After the reaction, the reaction mixture was extracted with toluene. The extract was washed with water and dried. Toluene was evaporated, and the residue was recrystallized from acetone to give 35.2 g (0.707 mole) of a compound of the following formula.

Yield: 70.7%
Transition temperatures: 120° C. (C→S)
122° C. (S⇌N)
267° C. (N⇌I)

EXAMPLE 8

By the same procedure as in Example 7, the following compound was obtained.

Yield: 72.4%
Transition temperatures: 113° C. (C→S)
117° C. (S⇌N)
269° C. (N⇌I)

EXAMPLE 9

By the same procedure as in Example 7, the following compound was obtained.

Yield: 71.4%
Transition temperatures: 112° C. (C→S)
116° C. (S⇌N)
269° C. (N⇌I)

EXAMPLE 10

By the same procedure as in Example 7, the following compound was obtained.

Yield: 69.7%
Transition temperatures: 113° C. (C→S)
121° C. (S⇌N)
264° C. (N⇌I)

EXAMPLE 11

By the same procedure as in Example 7, the following compound was obtained.

Yield: 70.2%
Transition temperatures: 108° C. (C→S)
111° C. (S⇌N)
258° C. (N⇌I)

EXAMPLE 12

By the same procedure as in Example 7, the following compound was obtained.

Yield: 72.2%
Transition temperatures: 117° C. (C→S)
125° C. (S⇌N)
274° C. (N⇌I)

EXAMPLE 13

By the same procedure as in Example 7, the following compound was obtained.

Yield: 70.1%
Transition temperatures: 112° C. (C→S)
118° C. (S⇌N)
268° C. (N⇌I)

EXAMPLE 14

20.4 g (0.100 mole) of a compound of the formula and 30.3 g (0.100 mole) of a compound of the formula were dissolved in 200 ml of toluene, and with stirring at room temperature, 15.8 g (0.200 mole) of pyridine was added dropwise. After the addition, the mixture was refluxed for 2 hours. After the reaction, the reaction mixture was extracted with toluene. The extract was washed with wafter, and dried. Toluene was evaporated, and the residue was recrystallized from acetone to give 33.7 g (0.0717 mole) of a compound of the following formula.

Yield: 71.7%
Transition temperatures: 139° C. (C→S)
141° C. (S⇌N)
289° C. (N⇌I)

EXAMPLE 15

By the same procedure as in Example 14, the following compound was obtained.

Yield: 73.7%
Transition temperatures: 133° C. (C→S)
136° C. (S⇌N)
291° C. (N⇌I)

EXAMPLE 16

By the same procedure as in Example 14, the following compound was obtained.

n-C₃H₇—◯—COO—◯—COO—◯—⟨H⟩—n-C₅H₁₁

Yield: 74.1%
Transition temperatures: 138° C. (C→S)
146° C. (S⇌N)
293° C. (N⇌I)

EXAMPLE 17

By the same procedure as in Example 14, the following compound was obtained.

n-C₄H₉—◯—COO—◯—COO—◯—⟨H⟩—C₂H₅

Yield: 70.9%
Transition temperatures: 127° C. (C→S)
130° C. (S⇌N)
280° C. (N⇌I)

EXAMPLE 18

By the same procedure as in Example 14, the following compound was obtained.

n-C₄H₉—◯—COO—◯—COO—◯—⟨H⟩—n-C₃H₇

Yield: 72.4%
Transition temperatures: 132° C. (C→S)
135° C. (S⇌N)
292° C. (N⇌I)

EXAMPLE 19

By the same procedure as in Example 14, the following compound was obtained.

Yield: 71.2%
Transition temperatures: 133° C. (C→S)
140° C. (S⇌N)
287° C. (N⇌I)

EXAMPLE 20

By the same procedure as in Example 14, the following compound was obtained.

Yield: 70.5%
Transition temperatures: 132° C. (C→S)
137° C. (S⇌N)
290° C. (N⇌I)

EXAMPLE 21

28.0 g (0.100 mole) of a compound of the formula and 18.9 g (0.100 mole) of the formula were dissolved in 200 ml of toluene, and with stirring at room temperature, 15.8 g (0.200 mole) of pyridine was added dropwise. After the addition, the mixture was refluxed for 2 hours. After the reaction, the reaction mixture was extracted with toluene. The extract was washed with water and dried. Toluene was evaporated, and the residue was recrystallized from acetone to give 32.8 g (0.0759 mole) of a compound of the following formula.

Yield: 75.9%
Transition temperatures: 186° C. (C→S)
189° C. (S⇌N)
308° C. (N⇌I)

EXAMPLE 22

By the same procedure as in Example 21, the following compound was obtained.

Yield: 76.2%
Transition temperatures: 194° C. (C→S)
214° C. (S⇌N)
319° C. (N⇌I)

EXAMPLE 23

By the same procedure as in Example 21, the following compound was obtained.

Yield: 73.8%
Transition temperatures: 190° C. (C→S)
203° C. (S⇌N)
313° C. (N⇌I)

EXAMPLE 24

By the same procedure as in Example 21, the following compound was obtained.

Yield: 75.4%
Transition temperatures: 191° C. (C→S)
225° C. (S⇌N)
309° C. (N⇌I)

EXAMPLE 25

By the same procedure as in Example 21, the following compound was obtained.

Yield: 76.1%
Transition temperatures: 189° C. (C→S)
215° C. (S⇌N)
311° C. (N⇌I)

EXAMPLE 26

By the same procedure as in Example 21, the following compound was obtained.

Yield: 74.2%
Transition temperatures: 182° C. (C→S)
241° C. (S⇌N)
289° C. (N⇌I)

What is claimed is:
1. A nematic liquid crystalline compound selected from the group consisting of compounds represented by the general formula compounds represented by the general formula compounds represented by the general formula and compounds represented by the general formula wherein R and R', independently from each other, represent a linear alkyl group having 1 to 7 carbon atoms, and each cyclohexane ring is arranged in a trans-(equatorial-equatorial) form.

* * * * *